United States Patent
Darwal

(10) Patent No.: US 11,871,919 B2
(45) Date of Patent: Jan. 16, 2024

(54) TRANSNASAL ODONTOID RETRACTOR

(71) Applicant: Maureen Darwal, Montclair, NJ (US)

(72) Inventor: Maureen Darwal, Montclair, NJ (US)

( * ) Notice: Subject to any disclaimer, the term of this patent is extended or adjusted under 35 U.S.C. 154(b) by 0 days.

(21) Appl. No.: 15/940,225

(22) Filed: Mar. 29, 2018

(65) Prior Publication Data

US 2018/0280012 A1 Oct. 4, 2018

Related U.S. Application Data

(60) Provisional application No. 62/478,057, filed on Mar. 29, 2017.

(51) Int. Cl.
*A61B 17/02* (2006.01)
*A61B 17/29* (2006.01)
*A61B 17/00* (2006.01)
*A61B 17/24* (2006.01)

(52) U.S. Cl.
CPC ........ *A61B 17/025* (2013.01); *A61B 17/0218* (2013.01); *A61B 17/2909* (2013.01); *A61B 17/24* (2013.01); *A61B 2017/00278* (2013.01); *A61B 2017/00407* (2013.01); *A61B 2017/0256* (2013.01); *A61B 2217/005* (2013.01)

(58) Field of Classification Search
CPC .................................................. A61B 17/025
USPC .................................................. 600/201–245
See application file for complete search history.

(56) References Cited

U.S. PATENT DOCUMENTS

| | | | | |
|---|---|---|---|---|
| 3,019,790 | A * | 2/1962 | Militana | A61B 17/122 606/108 |
| 4,841,959 | A | 6/1989 | Ransford | |
| 5,037,430 | A * | 8/1991 | Hasson | A61B 17/42 606/119 |
| 5,704,925 | A * | 1/1998 | Otten | A61B 17/00234 604/115 |
| 6,248,061 | B1 * | 6/2001 | Cook, Jr. | A61B 1/267 600/187 |
| 6,436,117 | B1 * | 8/2002 | Waller | A61B 17/320016 606/167 |
| 7,153,321 | B2 * | 12/2006 | Andrews | A61B 17/0206 606/205 |
| 8,377,049 | B2 * | 2/2013 | Cho | A61B 17/2812 606/15 |
| 9,155,633 | B2 | 10/2015 | Cloutier et al. | |
| 2002/0058965 | A1 * | 5/2002 | Andrews | A61B 17/0206 606/205 |
| 2004/0068291 | A1 * | 4/2004 | Suzuki | A61B 10/0096 606/205 |
| 2005/0154263 | A1 * | 7/2005 | Nady | A61B 1/32 600/210 |
| 2007/0250100 | A1 * | 10/2007 | Schon | A61M 25/0668 606/191 |
| 2009/0018399 | A1 * | 1/2009 | Martinelli | A61B 5/0488 600/210 |
| 2011/0313323 | A1 | 12/2011 | Henderson et al. | |
| 2012/0035638 | A1 * | 2/2012 | Mathaneswaran | A61B 1/32 606/170 |

(Continued)

*Primary Examiner* — Eduardo C Robert
*Assistant Examiner* — Tara Rose E Carter
(74) *Attorney, Agent, or Firm* — IP Strategies

(57) ABSTRACT

This disclosure provides a transnasal odontoid retractor that can retract tissue unilaterally or bilaterally, with the retractor including one or more retractor shafts that can be configured between a closed position and an open position, and controlled using, for example, a forcep.

7 Claims, 4 Drawing Sheets

(56) References Cited

U.S. PATENT DOCUMENTS

2015/0065809 A1* 3/2015 Assia ................ A61B 17/0231
600/217

* cited by examiner

ND RETRACTOR

TRANSNASAL ODONTOID RETRACTOR

This application claims priority from U.S. Provisional Patent Application No. 62/478,057, which was filed on Mar. 29, 2017, which application is hereby incorporated herein by reference in its entirety.

BACKGROUND

During superior anterior cervical approaches through transnasal route during surgeries such as odontoidectomy for basilar invagination, resection of anterior cervical spinal cord lesions or tumors as well as chordomas, the posterior wall of the nasal pharynx/basopharyngeal fascia and the atlantooccipotal membrane, longus capitis muscle, and longus coli muscles are incised and attempted to be retracted with suction, while manipulating bony areas. One issue which occurs during these procedures, is that the surgeon's field of view is obstructed by the nasal pharynx wall. The obstructed view can result in longer surgeries and a higher risk of complications.

To overcome this issue, a surgeon typically will use suction to retract the tissue on either side as well as using the suction to remove bony debris or blood. Retracting using the suction, however, can only be used unilaterally (one fold is retracted), thus the view of the odontoid is still obstructed.

SUMMARY

This disclosure provides a transnasal odontoid retractor that can retract tissue unilaterally or bilaterally, the retractor can include one or more retractor shafts that can be controlled using, for example, a forcep. The retractor can also be removably attached to a suction. Further the retractor can include two shafts, where each shaft includes a retractor tip. In other embodiments the retractor can be built either integrally or removably from a suction.

DETAILED DESCRIPTION

Figure 1:
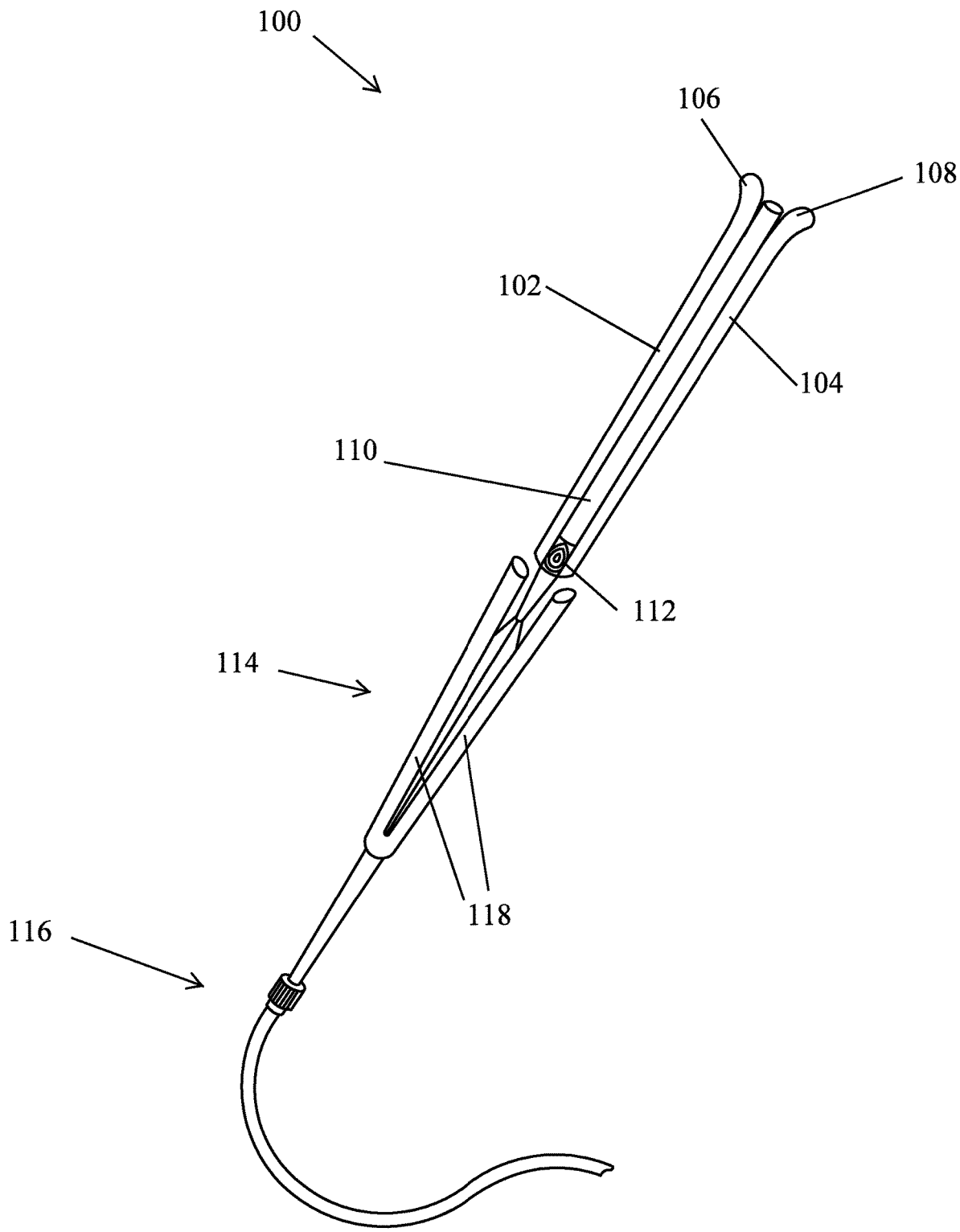
FIG. 1 is a perspective view of a retractor in accordance with an embodiment of this disclosure.

FIG. 1 is a perspective view of a retractor 100 according to an embodiment of the present disclosure. The retractor is in a closed position and includes two retractor shafts 102 and 104, with each shaft including a retractor tip 106 and 108, respectively. The tips 106 and 108 can provide the benefit of reducing the distance the retractor shaft is moved from a closed position. While FIG. 1 as well as other embodiments show the retractor tips 106 and 108, it should be understood that these tips are not required. Each retractor shaft 102 and 104 is positioned on the metal suction as shown. The retractor shafts 102 and 104 shown in the FIG. 1 are on opposing sides of the metal suction 110, but it will be understood that the retractor shafts 102 and 104 are not limited to this configuration. Further, in other embodiments there could be one retractor shaft or more than two. FIG. 1 also shows a teardrop shaped opening at the distal end of the suction 112, which a user manipulates to control the strength of suction, a distal forcep 114 for proximal control of the retractor shafts 102 and 104, and a distal suction tubing 116.

Figure 2:
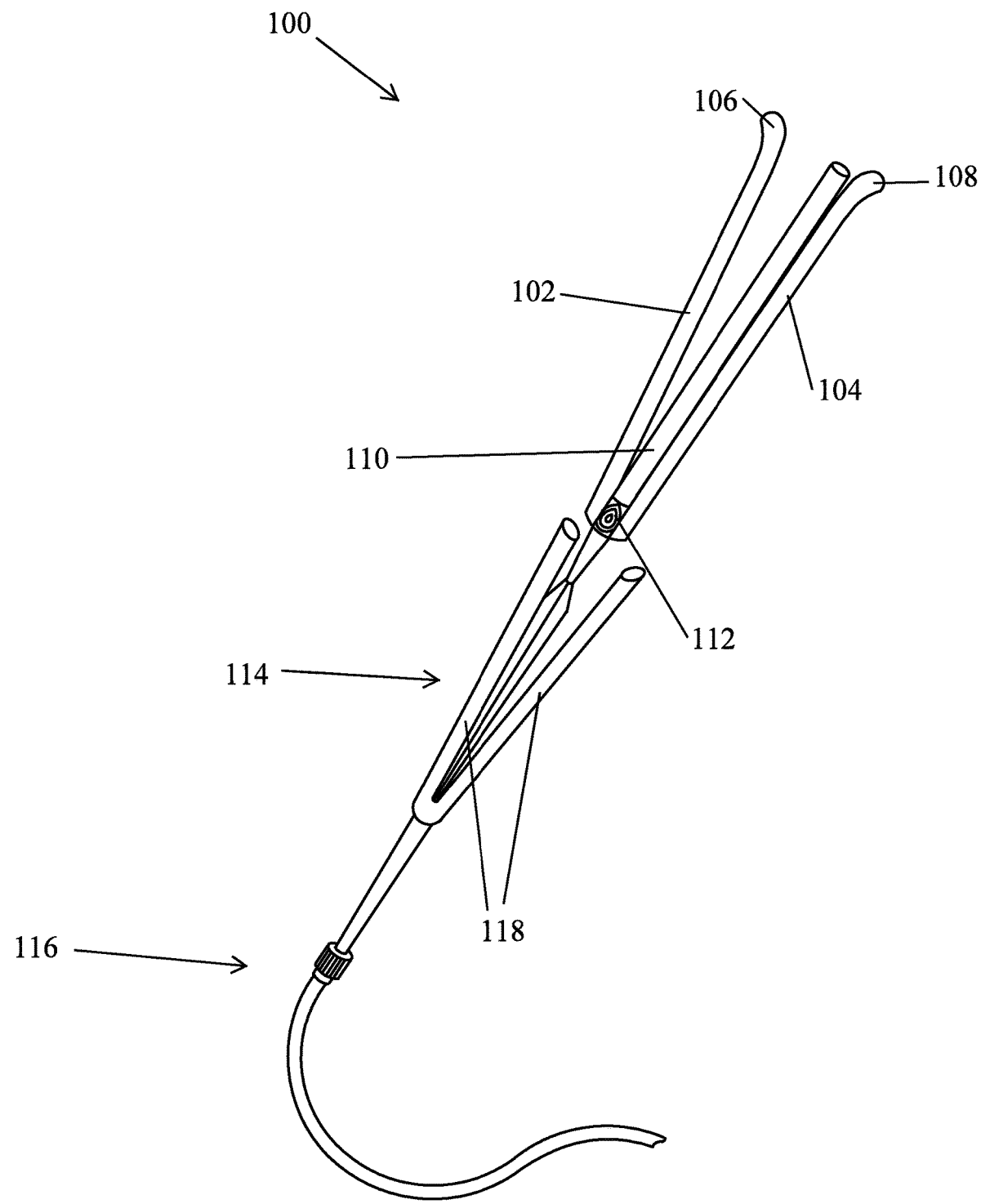
FIG. 2 is another perspective view of a retractor in accordance with another embodiment of this disclosure.
Figure 3:
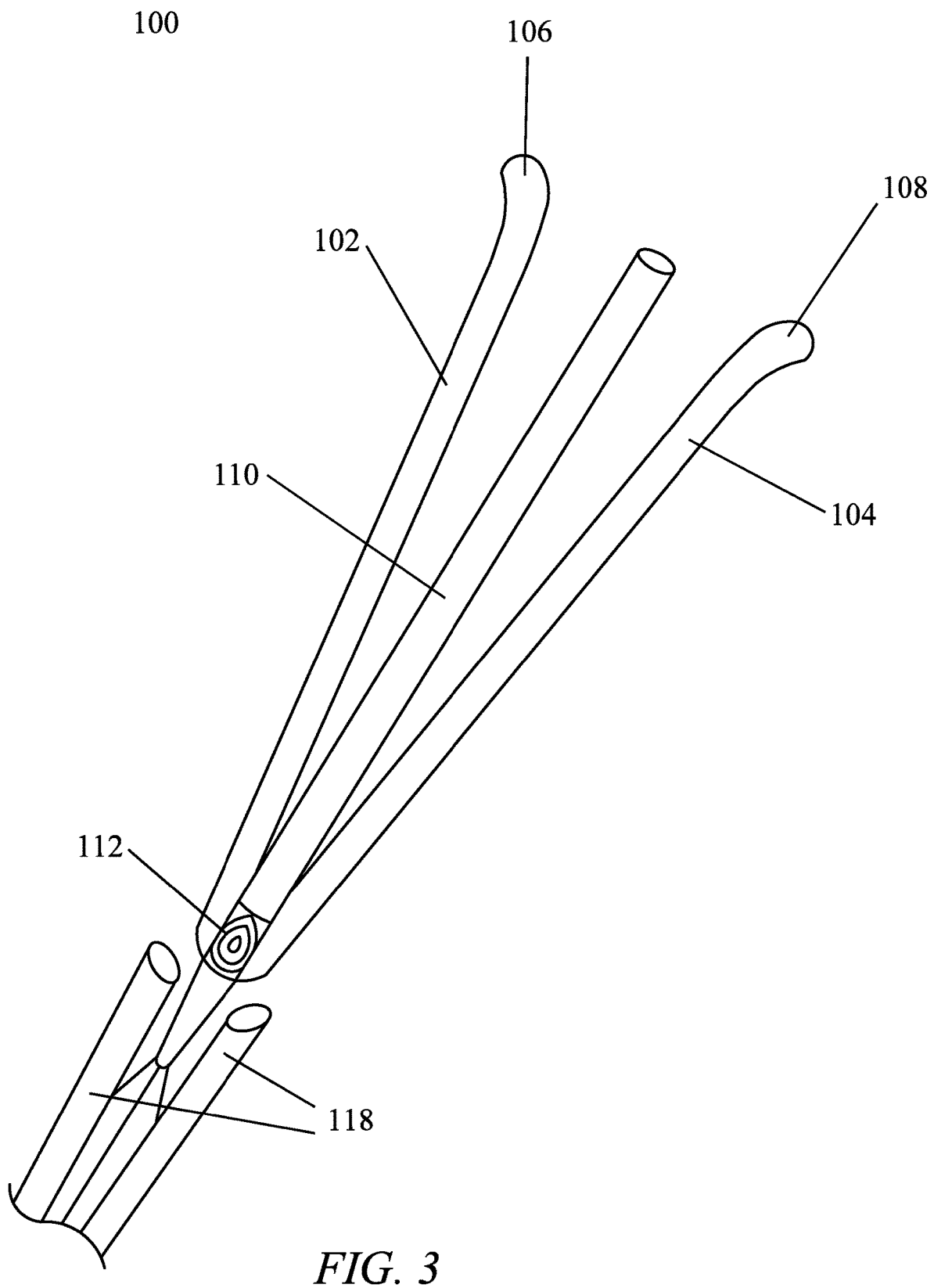
FIG. 3 is another perspective view of a retractor in accordance with another embodiment of this disclosure.

A user grasps handles of the distal forcep 114 to control one or more retractor shafts 102 and 104. Specifically, pressing the handles 118 moves one or more retractor shafts from a closed position as shown in FIG. 1 to an open position shown in FIGS. 2 and 3. In FIG. 2 for example, one of the handles of the distal forcep 114 is pressed, which opens a corresponding retractor shaft 102. The retractor shaft 102 in this embodiment would be an ipsilateral retractor shaft. FIG. 3 illustrates bilateral retraction where the retractor shafts 102 and 104 are in an open position when both handles of the distal forcep 114 is pressed. It should be understood by persons having ordinary skill that one handle of the distal forcep 114 can be employed to open both retractor shafts 102 and 104 without departing from the scope of this disclosure.

Figures 4A, 4B:
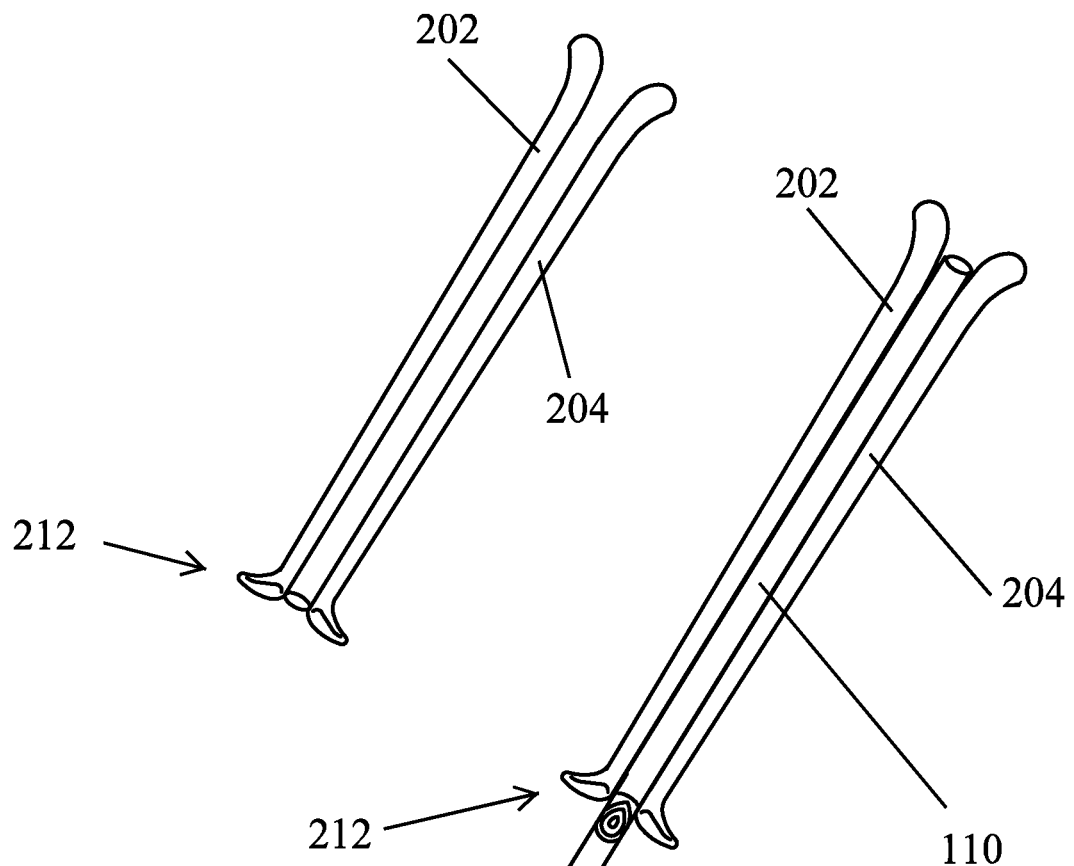
FIG. 4A is another perspective view of a removable retractor shaft and another retractor according to additional embodiments of this disclosure.
FIG. 4B is another perspective view of a retractor in accordance with another embodiment of this disclosure.

FIG. 4A illustrates another embodiment according to this disclosure. Shown in FIG. 4 are retractor shafts 202 and 204 that can be applied to a metal suction 210. The shafts 202 and 204 fit over the suction 210 as shown in FIG. 4B. In a non-limiting example, the retractor can slide over a 7 LL or 9 LL suction tube that is 15 cm to 17 cm in length. A user can move the shafts to an open position by manipulating a bilateral unidirectional cam ratchet 212. The shafts 202 and 204 can return to the closed position through the use of a release mechanism. While a bilateral unidirectional cam ratchet 212 is shown in FIG. 4, it should be understood that other known ways of moving the shafts from a closed to an open position and vice versa falls within the scope of this disclosure.

In the embodiments described herein, the working length of the retractor can be 13 cm to 15 cm, and the total width of the retractor when in the bilateral open position (i.e., both retractor shafts are open) can be 1.5 cm at maximum diameter. The suction tubes described herein can be a 7 or 9 French diameter with 15 cm to 17 cm length. It should be understood that other dimensions can be employed without departing from the scope of this disclosure. In addition, the suction hole can be a tear-drop shape, or other suitable configuration for controlling suction.

While embodiments have been illustrated and described herein, it is appreciated that various substitutions and changes in the described embodiments may be made by those skilled in the art without departing from the spirit of this disclosure. The embodiments described herein are for illustration and not intended to limit the scope of this disclosure. For example, while the retractor herein has, in some embodiments, been characterized as a transnasal odontoid retractor, it should be understood that the embodiments described can be used in other surgical applications such as, without limitation, transsphenoidal surgery, trans-ethmoid surgery, endoscopic strip craniectomy, keyhole craniotomy.

The invention claimed is:

1. A device for unilateral or bilateral retraction of tissue comprising:
   at least one retractor shaft configured to be positioned in a closed position and an open position;
   a forcep including at least one handle, where said forcep is configured to control the at least one retractor shaft from the closed position to the open position; and
   a suction having an opening at a distal end of the suction configured to allow control of a strength of the suction, wherein said at least one retractor shaft maintains a direct connection to said suction when the at least one retractor shaft moves from said closed position to said open position and moves from said open position to said closed position, and wherein at least a portion of the retractor shaft extends away from the suction when the retractor shaft moves from said closed position to said open position.

2. The device of claim 1 further comprising at least a second retractor shaft directly connected to the suction, wherein said forcep controls the retractor shafts from the closed position to the open position.

3. The device of claim 2 wherein the forceps include two handles.

4. The device of claim 2 wherein said retractor shafts are removably attached to said suction.

5. The device of claim 2 wherein said retractor shafts are positioned bilaterally on the suction.

6. The device of claim 1 wherein said at least one retractor shaft includes a retractor tip.

7. The device of claim 1 wherein said retractor shaft positioned ipsilaterally on the suction.

* * * * *